(12) United States Patent
Diaz et al.

(10) Patent No.: US 10,433,990 B2
(45) Date of Patent: Oct. 8, 2019

(54) INTRODUCER WITH SIDE OPENING

(71) Applicant: COOK MEDICAL TECHNOLOGIES LLC, Bloomington, IN (US)

(72) Inventors: Nuno Diaz, Malmo (SE); Blayne A. Roeder, Bloomington, IN (US); Siddharth Vad, Irvine, CA (US); Stephan Haulon, Lille (FR)

(73) Assignee: Cook Medical Technologies LLC, Bloomington, IN (US)

( * ) Notice: Subject to any disclaimer, the term of this patent is extended or adjusted under 35 U.S.C. 154(b) by 744 days.

(21) Appl. No.: 14/978,666

(22) Filed: Dec. 22, 2015

(65) Prior Publication Data

US 2016/0175128 A1   Jun. 23, 2016

Related U.S. Application Data

(60) Provisional application No. 62/096,038, filed on Dec. 23, 2014.

(51) Int. Cl.
*A61F 2/95* (2013.01)
*A61F 2/954* (2013.01)
*A61F 2/966* (2013.01)

(52) U.S. Cl.
CPC .............. *A61F 2/95* (2013.01); *A61F 2/954* (2013.01); *A61F 2/966* (2013.01)

(58) Field of Classification Search
CPC .. A61F 2/95; A61F 2/954; A61F 2/966; A61F 2/962; A61F 2002/9505;

(Continued)

(56) References Cited

U.S. PATENT DOCUMENTS

| 6,524,335 B1 | 2/2003 | Hartley et al. |
| 7,645,298 B2 | 1/2010 | Hartley et al. |

(Continued)

FOREIGN PATENT DOCUMENTS

| EP | 0 699 451 A2 | 3/1996 |
| EP | 2 777 606 A1 | 9/2014 |

OTHER PUBLICATIONS

Extended European Search Report for related patent application No. EP 15 27 5275.4-1662; 7 pgs; dated May 3, 2016.

*Primary Examiner* — Erich G Herbermann
(74) *Attorney, Agent, or Firm* — Brinks Gilson & Lione

(57) ABSTRACT

An introducer for an endoluminal prosthesis and a methods for delivering a prosthesis within a body vessel are described. The introducer comprises pusher catheter having a lumen extending therethrough, the lumen being in communication with an opening formed in the sidewall of the pusher. A sheath is disposed over the pusher catheter and also has an opening formed in its sidewall. The sheath is longitudinally movable relative to the pusher catheter between a prosthesis delivery position and a prosthesis deployment position. When the sheath is in the deployment position, the opening formed in the sidewall of the pusher catheter is at least partially longitudinally aligned with the opening formed in the sidewall of the sheath. A wire may extend though the opening in the sheath, the opening in the pusher, through the lumen of the pusher and through a fenestration in a prosthesis to cannulate a branch vessel.

12 Claims, 16 Drawing Sheets

(58) Field of Classification Search
CPC ...... A61F 2002/9511; A61F 2002/9522; A61F 2002/9665; A61M 25/0015; A61M 25/09; A61M 2025/1056
See application file for complete search history.

(56) References Cited

U.S. PATENT DOCUMENTS

| | | |
|---|---|---|
| 8,167,926 B2 | 5/2012 | Hartley et al. |
| 8,172,895 B2 | 5/2012 | Anderson et al. |
| 8,740,964 B2 | 6/2014 | Hartley |
| 8,870,939 B2 | 10/2014 | Roeder et al. |
| 8,876,879 B2 | 11/2014 | Hartley et al. |
| 8,911,488 B2 | 12/2014 | Hartley et al. |
| 9,095,458 B2 | 8/2015 | Hartley et al. |
| 9,173,756 B2 | 11/2015 | Hopkins et al. |
| 2002/0133118 A1 | 9/2002 | Gerdts |
| 2005/0090890 A1* | 4/2005 | Wu .......... A61F 2/95 623/1.11 |
| 2008/0009937 A1 | 1/2008 | Kipperman |
| 2011/0301685 A1* | 12/2011 | Kao .......... A61F 2/95 623/1.11 |
| 2012/0095567 A1* | 4/2012 | Weisman .......... A61F 2/95 623/23.7 |

* cited by examiner

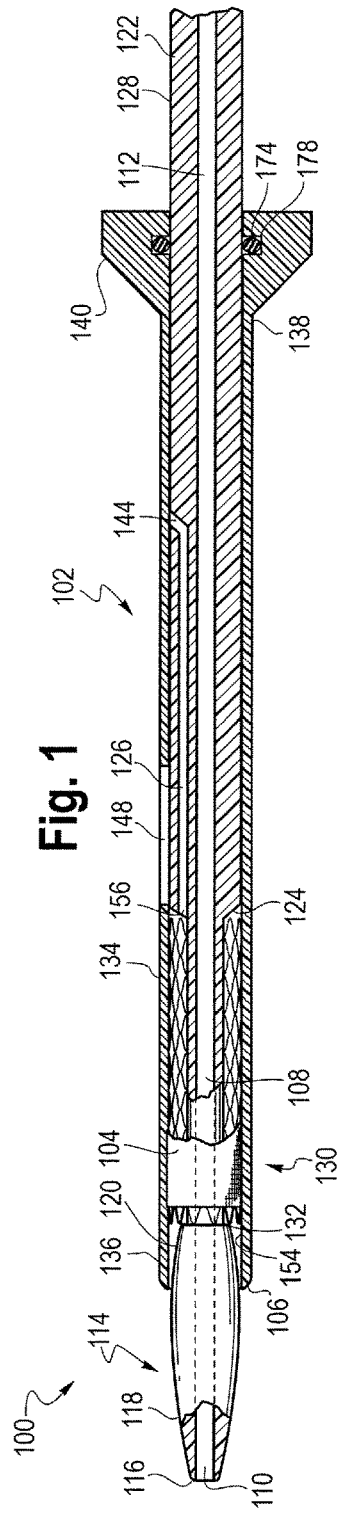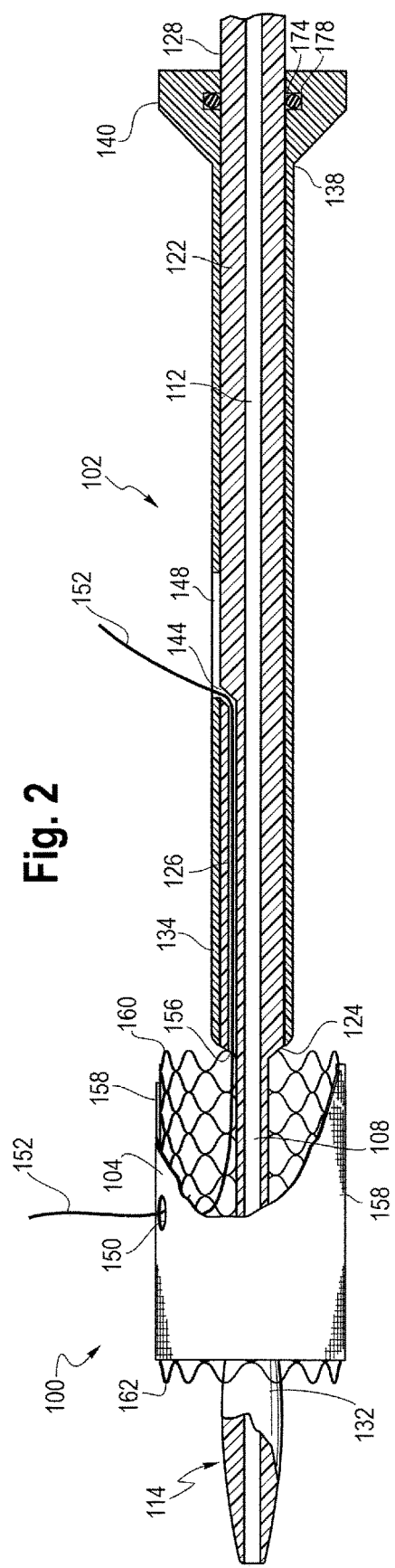

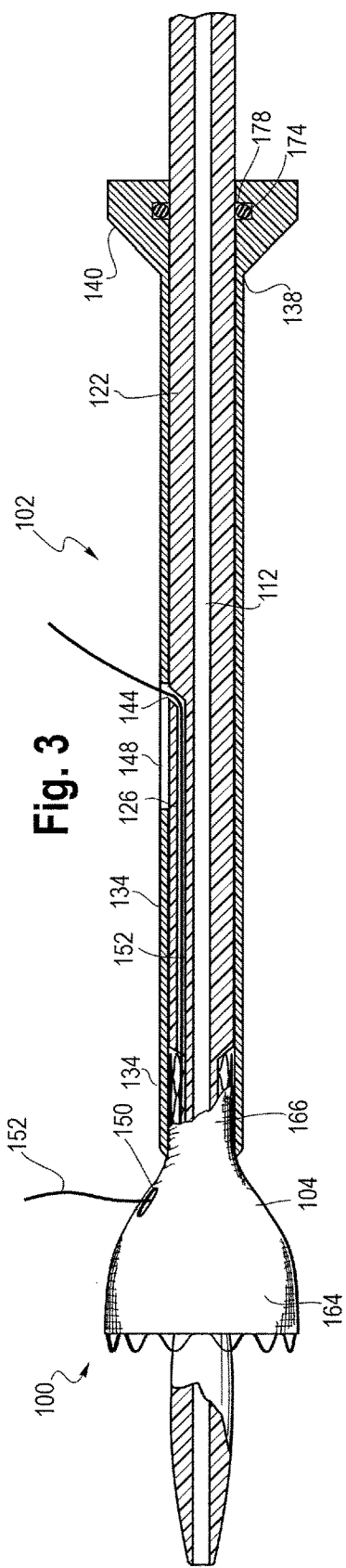

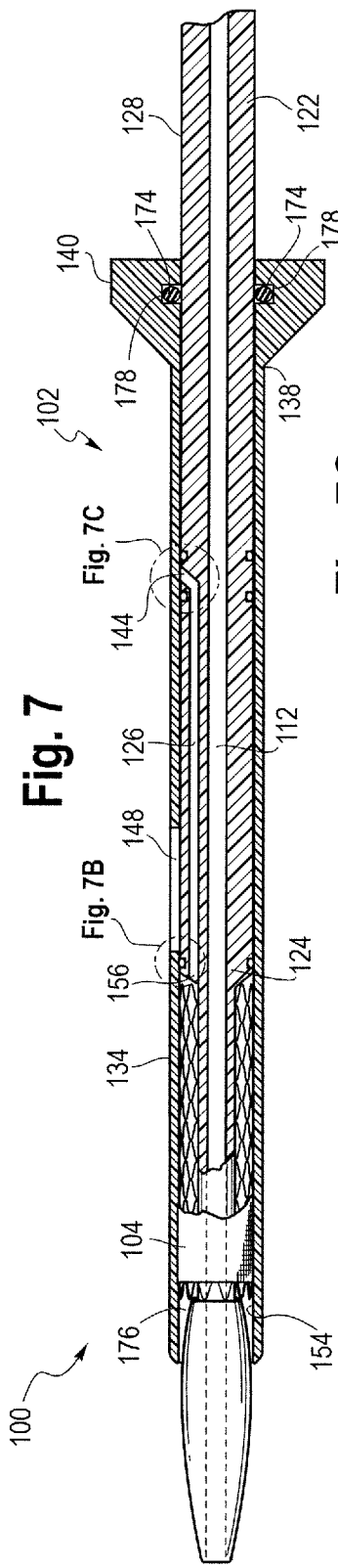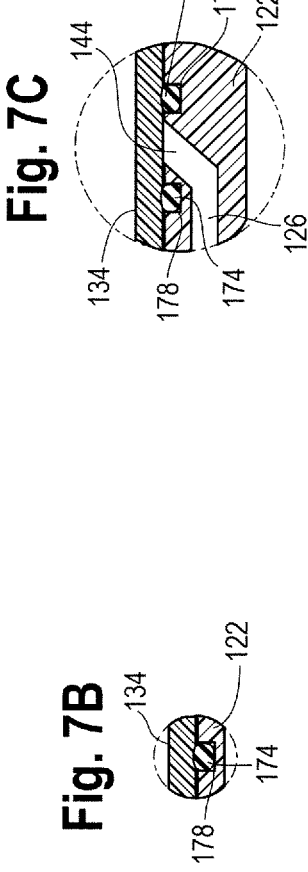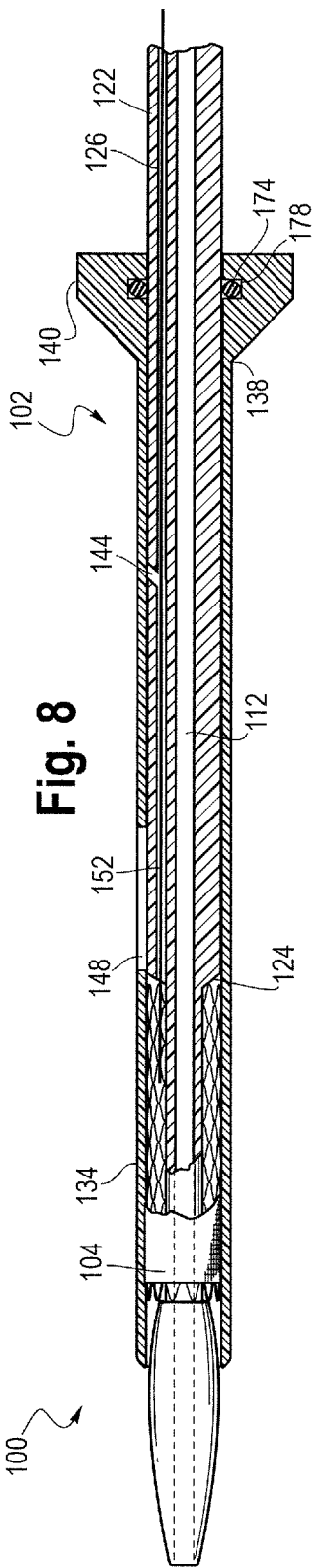

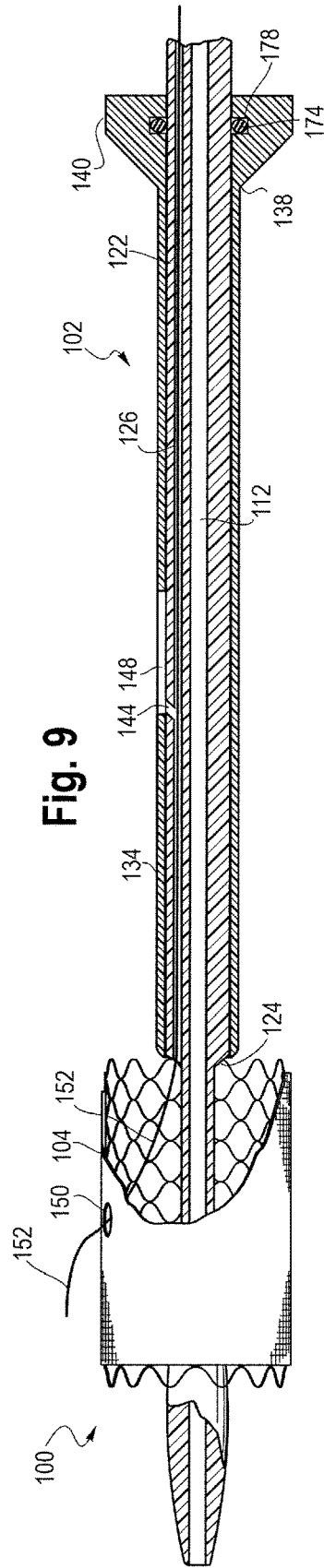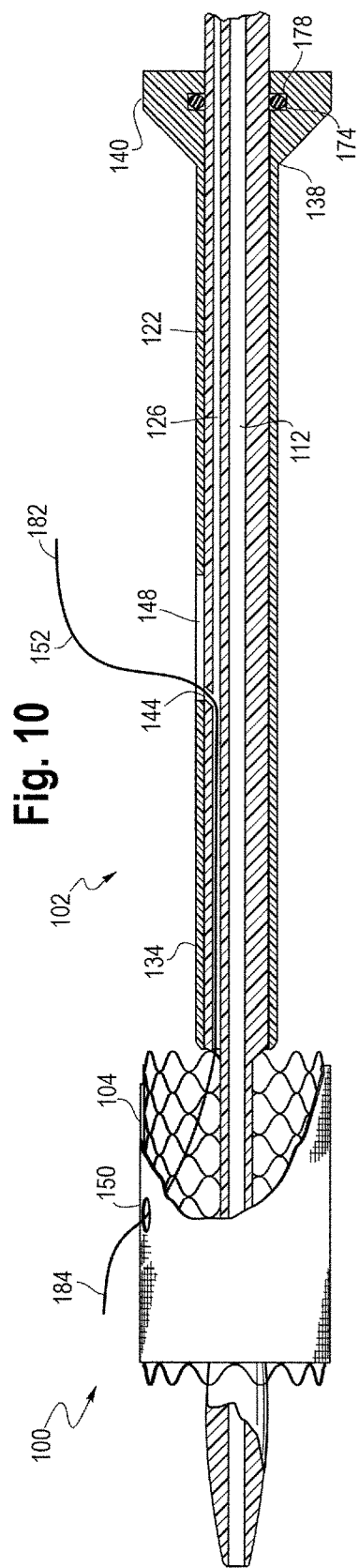

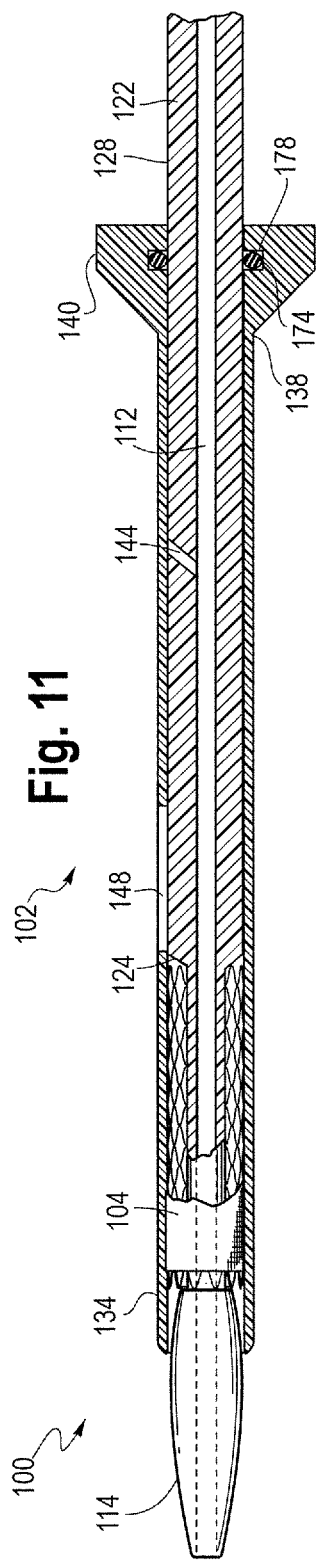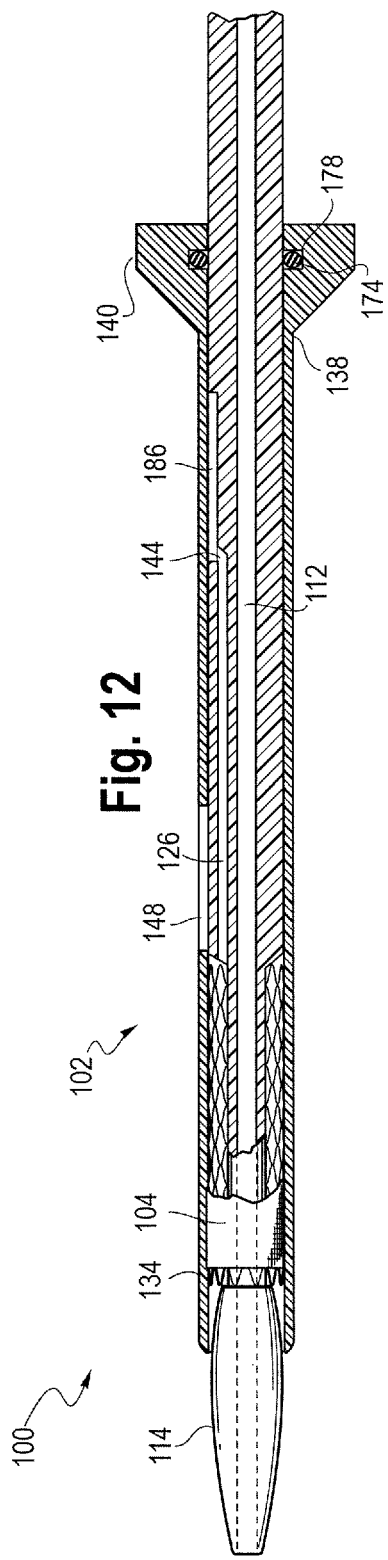

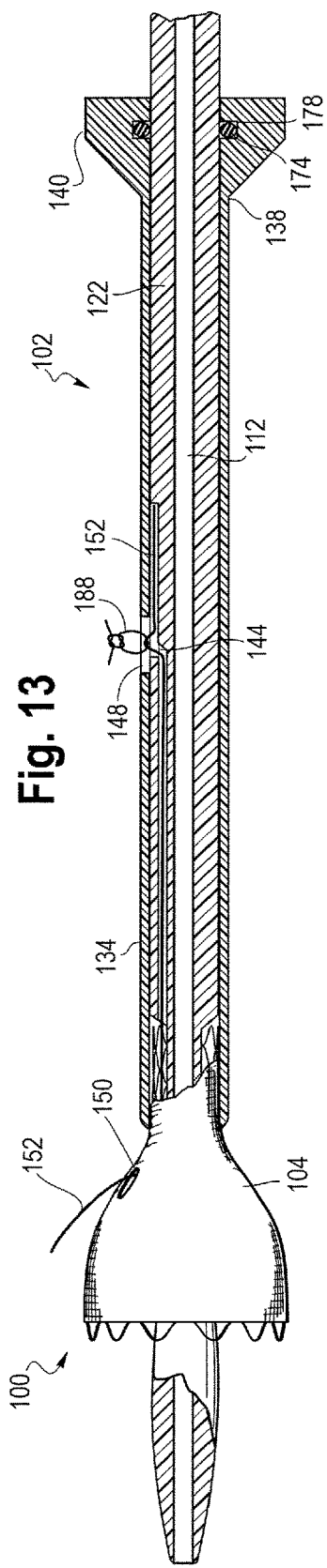
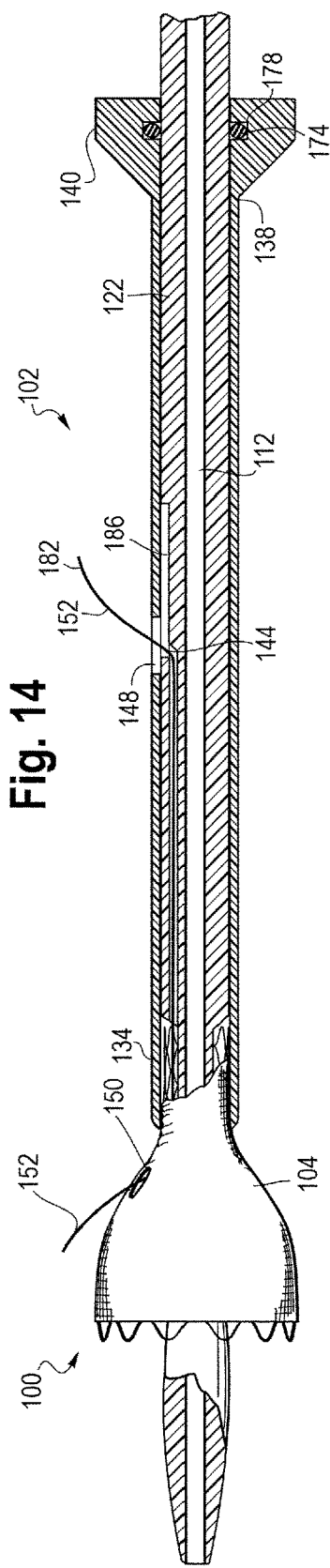

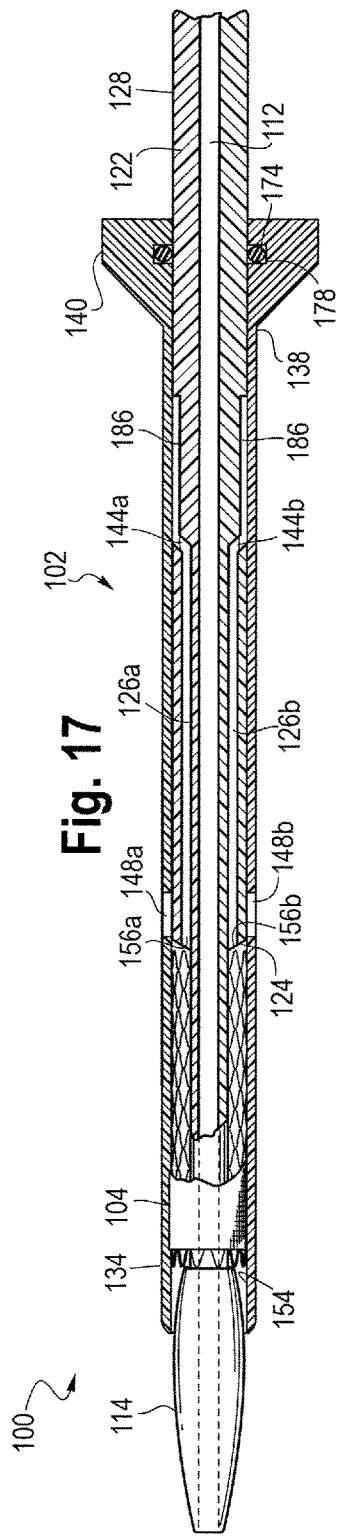
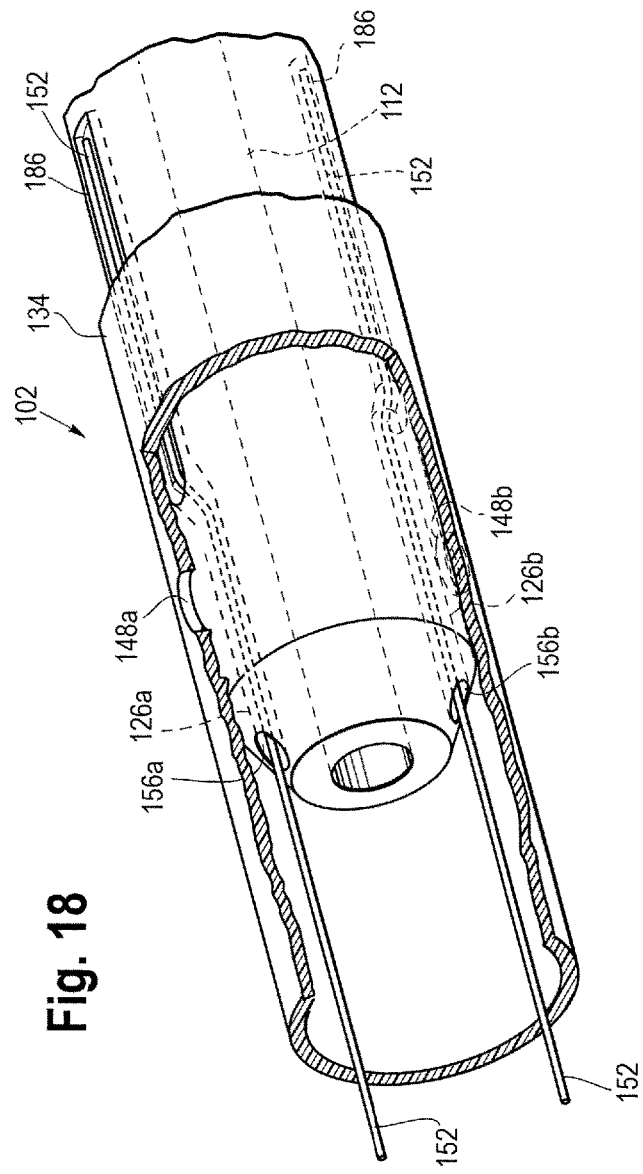
Fig. 17
Fig. 18

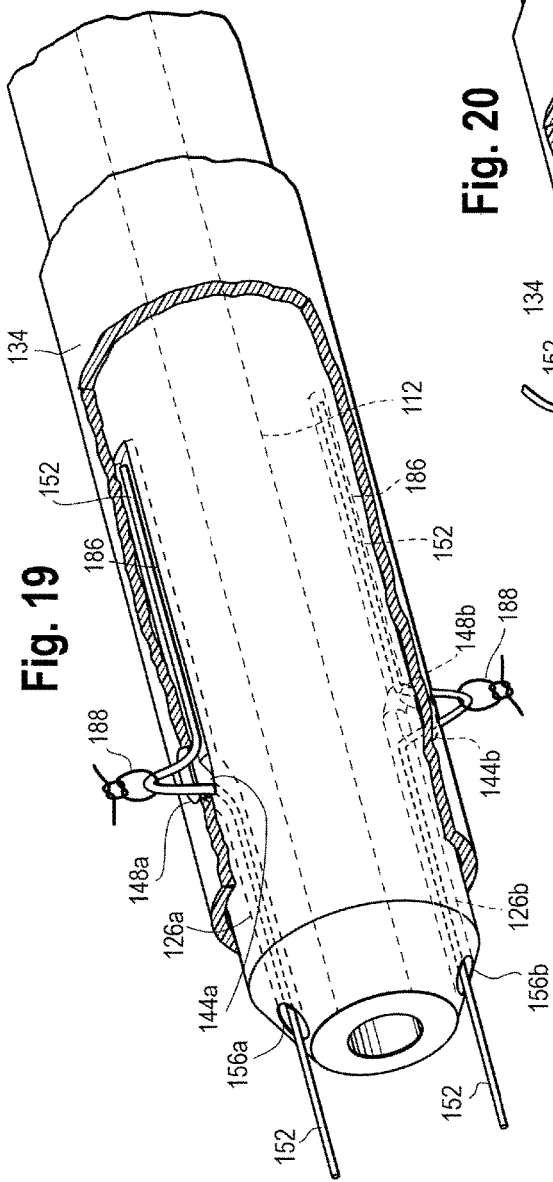
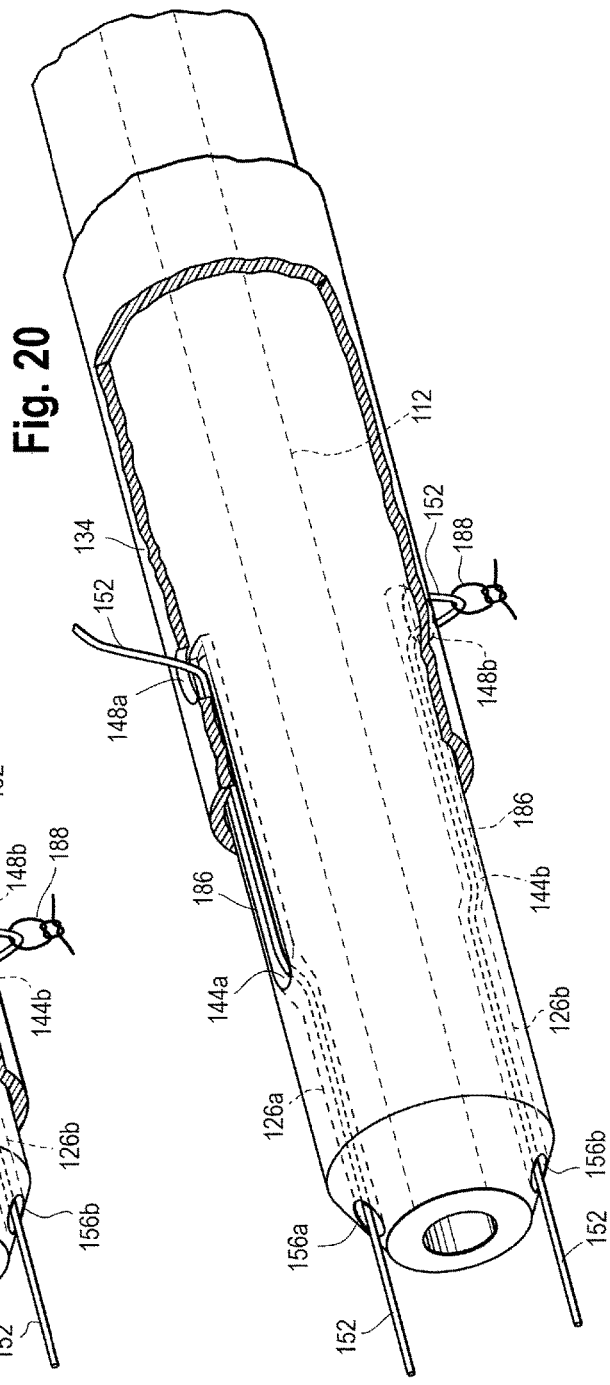

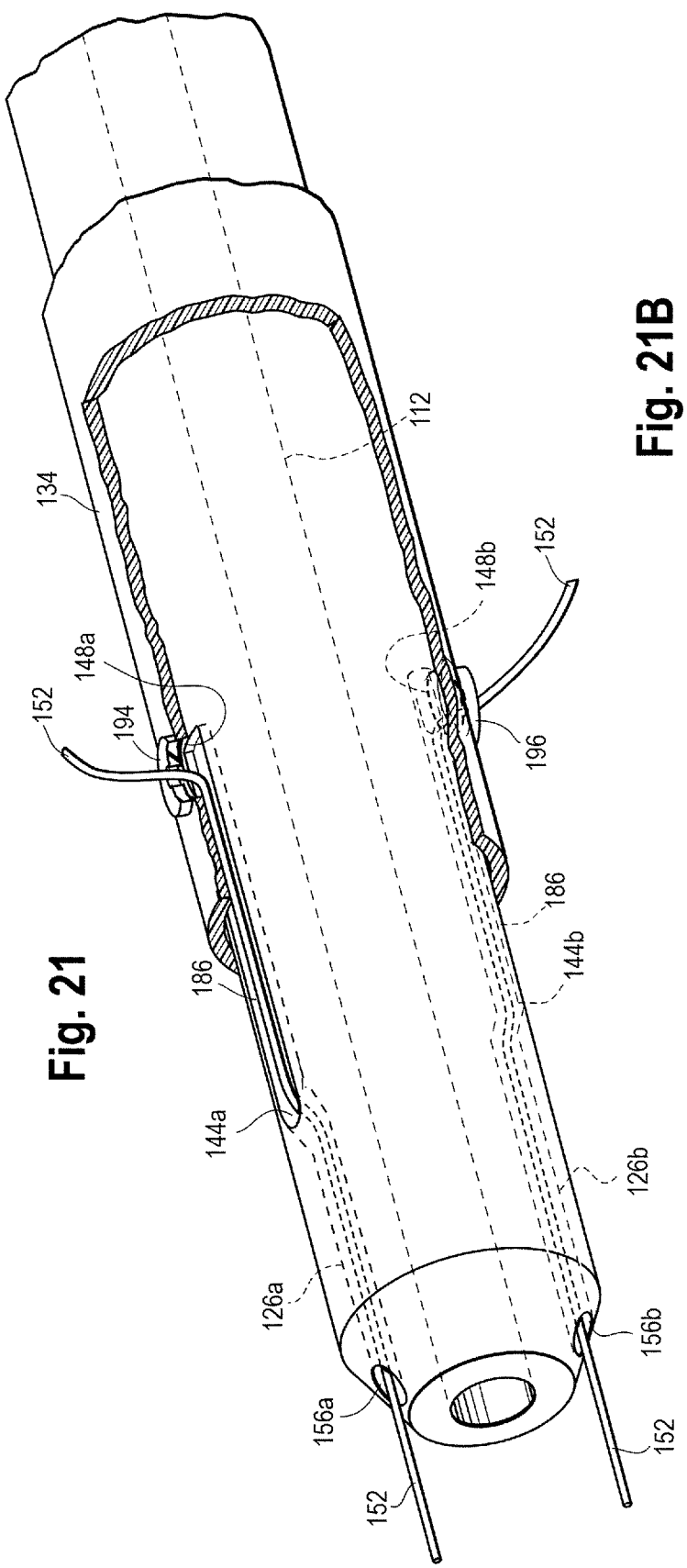
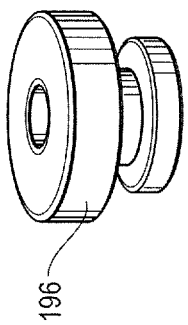
Fig. 21
Fig. 21B

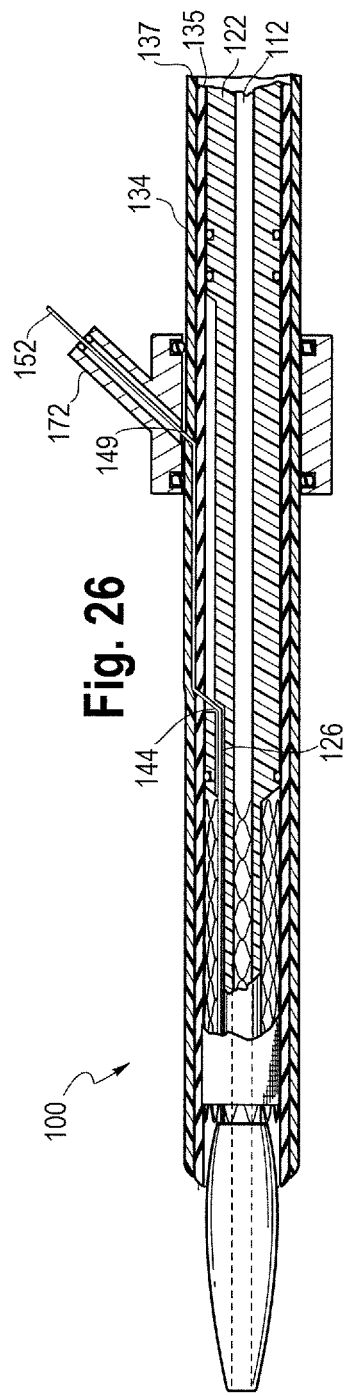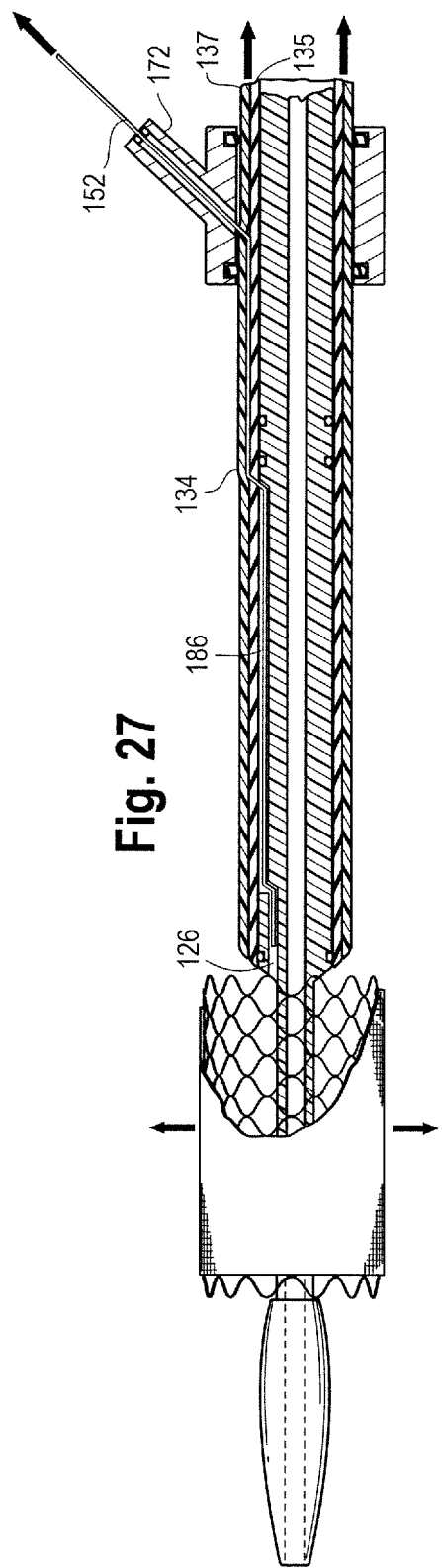

INTRODUCER WITH SIDE OPENING

CROSS REFERENCE TO RELATED APPLICATIONS

This application claims the benefit of U.S. Provisional Application No. 62/096,038 filed on Dec. 23, 2014, the entire contents of which are hereby incorporated by reference.

TECHNICAL FIELD

This disclosure relates to medical devices and more particularly to introducers and systems for implanting a prosthesis within a human or animal body for repair of damaged vessels, ducts or other physiological pathways.

BACKGROUND

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture.

Endovascular treatment of aortic aneurysms can be simplified by use of preloaded components such as wires, catheters, and/or sheaths. These preloaded components can be preloaded into a delivery system (e.g., into an introducer) and/or a prosthetic device prior to introduction into a patient to aid in delivery of additional prosthetic devices (e.g., branch extension prostheses) into the main prosthetic device. These preloaded components may help to simplify branch vessel cannulation, shorten procedural times, and/or provide improved outcomes for patients.

In some pre-loaded introducers, the sheath, guide wire and/or catheter often extend substantially the entire length of the introducer, between the proximal and distal ends. As such, one or more of these pre-loaded components are typically required to be a relatively greater length than the introducer so as to extend along the length of the introducer, traverse the delivery system handle and still allow a sufficient working length to access target arteries. A pre-loaded delivery system and method is described herein that shortens one or more of the pre-loaded components as well as shorten the overall length of the delivery system while simplifying branch vessel cannulation, shorten procedural times and provide better patient outcomes, among other advantages.

SUMMARY

An introducer for an endoluminal prosthesis and methods for delivering a prosthesis to a target site within a body vessel with an introducer are described herein.

Disclosed here is an introducer for an endoluminal prosthesis comprises an inner cannula having a proximal end and a distal end and a prosthesis releasably attached to the proximal end of the inner cannula. A pusher catheter is disposed about at least a portion of the inner cannula, the pusher catheter having a proximal end a distal end and a side wall extending between the proximal and distal ends, the side wall comprising an opening formed in the side wall. A lumen extends at least partially through the pusher catheter between the proximal and distal ends of the pusher catheter, with the pusher catheter lumen is in communication with the opening formed in the side wall of the pusher catheter. A tubular sheath is disposed coaxially about at least a portion of the pusher catheter, the tubular sheath having a proximal end, a distal end, a sidewall extending between the proximal and distal ends of the sheath and an opening formed in the sheath sidewall. The sheath is longitudinally movable relative to the pusher catheter between a prosthesis delivery position and a prosthesis deployment position, such that when the sheath is in the prosthesis deployment position, the opening formed in the sidewall of the pusher catheter is at least partially longitudinally aligned with the opening formed in the sidewall of the sheath.

A method of using an endoluminal prosthesis introducer also is described. In one example, the method comprises providing an introducer comprising an inner cannula having a proximal end and a distal end and a prosthesis releasably attached to the proximal end of the inner cannula. A pusher catheter is disposed about at least a portion of the inner cannula, the pusher catheter having a proximal end a distal end and a sidewall extending between the proximal and distal ends. The sidewall of the pusher catheter has an opening formed in the side wall. A lumen extends at least partially through the pusher catheter between the proximal and distal ends of the pusher catheter, with the pusher catheter lumen in communication with the opening formed in the side wall of the pusher catheter. A tubular sheath is disposed coaxially about at least a portion of the pusher catheter, the tubular sheath having a proximal end, a distal end, a sidewall extending between the proximal and distal ends of the sheath. An opening is formed in the sheath sidewall. The method comprises moving the sheath relative to the pusher catheter from a prosthesis delivery position to a prosthesis deployment position such that when the sheath is in the prosthesis deployment position, the opening formed in the sidewall of the sheath is at least partially aligned with the opening formed in the sidewall of the pusher catheter.

BRIEF DESCRIPTION OF THE DRAWINGS

FIG. 1 shows a longitudinal cross-sectional view of an exemplary delivery system for deploying a prosthesis within a body vessel.

FIG. 2 shows the system of FIG. 1 in a deployment configuration.

FIG. 3 shows the system of FIG. 1 in a partially deployed configuration.

FIG. 4 shows a longitudinal cross-sectional view of an exemplary delivery system for deploying a prosthesis within a body vessel.

FIG. 7 shows a longitudinal cross-sectional view of an exemplary delivery system for deploying a prosthesis within a body vessel.

FIG. 7B is an enlarged view of a portion of FIG. 7 showing a seal positioned adjacent to an opening in the sheath.

FIG. 7C is an enlarged view of a portion of FIG. 7 illustrating a seal positioned adjacent an opening formed in the pusher catheter.

FIG. 8 show a longitudinal cross-sectional view of an exemplary delivery system for deploying a prosthesis within a body vessel.

FIG. 9 shows the system of FIG. 8 in a deployment configuration.

FIG. 10 shows the system of FIG. 8 in a deployment configuration.

FIG. 11 shows a longitudinal cross-sectional view of an exemplary delivery system for deploying a prosthesis within a body vessel.

FIG. 12 shows a longitudinal cross-sectional view of an exemplary delivery system for deploying a prosthesis within a body vessel.

FIG. 13 shows the system of FIG. 12 in a partially deployed configuration.

FIG. 14 shows the system of FIG. 13 in a partially deployed configuration.

FIG. 17 shows a longitudinal cross-sectional view of an exemplary delivery system for deploying a prosthesis within a body vessel.

FIG. 18 shows a side-elevation partial cross-sectional view of the system of FIG. 17.

FIG. 19 shows a side-elevation partial cross-sectional view of the system of FIG. 17.

FIG. 20 shows a side-elevation partial cross-sectional view of the system of FIG. 17.

FIG. 21 shows a side-elevation partial cross-sectional view of the system of FIG. 17

FIG. 21B shows an enlarged view of the seal ring shown in FIG. 21.

FIG. 26 shows the system of FIG. 23 with a valve.

FIG. 27 shows the system of FIG. 26 in a deployment configuration.

DETAILED DESCRIPTION

Figure 5:
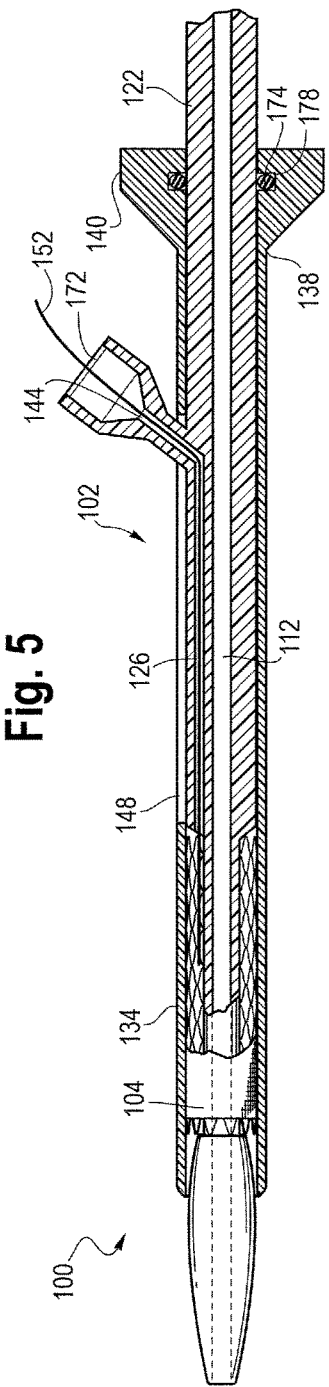
FIG. 5 shows the system of FIG. 4 with a valve.

The present disclosure relates to an endoluminal prosthesis for implantation within a human or animal body for repair of damaged vessels, ducts, or other physiological pathways and systems and methods for delivering such an endoluminal prosthesis. In the present disclosure, the term "proximal" refers to a direction that is away from a physician during a medical procedure, while the term "distal" refers to a direction that is closest to the physician during the procedure. In addition, like reference numbers throughout the various drawings designate similar structure.

FIG. 1 shows a longitudinal cross-sectional view of an exemplary delivery system 100 for deploying a prosthesis within a body vessel (not shown). Delivery system 100 includes an introducer 102 for delivering a prosthesis 104, such as an endovascular stent graft, stent, occlusion device or other implant to a body vessel. The introducer 102 has a proximal end 106 and a distal end (not shown). The distal end of the introducer may include an external manipulation section or handle (not shown) that remains outside of the patient during a procedure that can be gripped and manipulated by the user. Introducers suitable for use with the present invention include those shown and described in U.S. Pat. No. 8,876,879 to Hartley et al., in particular FIGS. 1-6 and the accompanying text, which patent is incorporated by reference herein in its entirety; U.S. Pat. No. 8,740,964 to Hartley et al., in particular FIGS. 1-8 and the accompanying text, which patent is incorporated by reference herein in its entirety; U.S. Pat. No. 8,911,488 to Hartley et al., in particular FIGS. 2-3 and the accompanying text, which patent is incorporated by reference herein in its entirety, and U.S. Pat. No. 9,173,756 to Hopkins et al., its figures and accompanying text, which patent is incorporated by reference herein in its entirety.

The stent graft 104 may be held in a radially inwardly or collapsed configuration within the delivery system 100 by a sheath 134. In the collapsed configuration, the stent graft has a reduced diameter delivery state allowing it to be delivered to a target location within a vessel or duct. The stent graft 104 also has an expanded deployed state in which it applies a radially outward force upon at least a portion of a vessel or duct, e.g., to maintain patency within a passageway or to hold open the lumen of a graft.

The stent graft 104 may be a generally tubular graft having one or more fenestrations 150 formed in a portion of the stent graft (see e.g. FIG. 2). One non-limiting example of a fenestrated prosthesis includes the Zenith Fenestrated AAA Endovascular Graft (Cook Medical, Bloomington, Ind.). The stent graft 104 may further comprise one or more branches or side arms extending from the fenestration(s) 150 (not shown). Suitable fenestrated stent grafts include those described and shown in Lennon et al., U.S. Pat. No. 8,172,895, Roeder et al., U.S. Pat. No. 8,870,939, Hartley, et al., U.S. Pat. No. 9,095,458, Hartley, et al., U.S. Pat. No. 7,645,298, Hartley, et al., U.S. Pat. No. 6,524,335, and Hartley, et al., U.S. Pat. No. 8,167,926, the disclosures of each of these incorporated by reference herein in their entireties.

An inner cannula 108 extends from the proximal end 106 to the distal end (not shown) of the introducer 102. The inner cannula 108 has a proximal end 110, a distal end (not shown), and an inner cannula lumen 112 extending there between and configured to receive a guide wire there through. A nose cone 114 may be disposed at the proximal end 110 of the inner cannula 108. The inner cannula 108 may extend into the nose cone 114 to the tip 116 of the nose cone 114. The nose cone 114 may be tapered and may have a long forward taper 118 and a shorter reverse taper 120. As such, the tip 116 presents an atraumatic surface to effectively navigate through a vessel lumen and the reverse taper 120 presents an atraumatic surface to prevent the nose cone 114 from snagging or catching on the stent graft 104 or other parts of the delivery system 100.

One or more pusher catheters 122 may be disposed over the inner cannula 108. The pusher catheter 122 has a proximal end 124, a distal end (not shown), a first pusher catheter lumen 126 and a side wall 128. The proximal end 124 of the pusher catheter 122 may be disposed distal to the nose cone 114. A stent graft retention region 130 for retaining the stent graft 104 onto the introducer 102 may be disposed between the distal end 132 of the nose cone 114 and the proximal end 124 of the pusher catheter 122. A removable or retractable sheath 134 may be disposed over the stent graft 104 and at least partially over the pusher catheter 122. The sheath 134 has a proximal end 136 and a distal end 138.

A manipulation region or handle 140 may be disposed at the distal end 138 of the sheath 134 and may be operatively attached to the sheath 134. A hemostatic valve (not shown) may be disposed within the handle 140. Suitable valves include, but are not limited to, those disclosed in U.S. Pat. No. 7,172,580 to Hruska et al., in particular that shown in FIG. 2 and described in the accompanying text, which disclosure is incorporated by reference in its entirety. Additionally or alternatively, one or more seals 174 may be disposed within the handle 140 to substantially reduce and/or prevent fluid backflow or leakage there through.

As shown in FIG. 1, the pusher catheter 122 has at least one opening 144 formed in the sidewall 128. The opening 144 opens into at least one lumen 126 in the pusher catheter 122. The lumen 126 may extend to a proximal opening 156 in the pusher catheter 122. The sheath 134 may also have one or more openings 148 formed therein. When in the un-deployed delivery position as shown in FIG. 1, a sidewall 154 of the sheath 134 can block the opening 144 in the pusher catheter 122. As such, the lumen 126 of the pusher catheter 112 is inaccessible when the system 100 is in the delivery configuration. For example, the lumen 126 may be fluidly isolated from the sheath opening 148 when in the delivery configuration of FIG. 1.

FIG. 2 shows the delivery system 100 of FIG. 1 with stent graft 104 in a radially outwardly expanded or deployed configuration. As previously mentioned, the stent graft 104 may have one or more fenestrations 150. Fenestration 150 may be configured and positioned at a location on the stent graft 104 to substantially align with the expected position of a branch vessel (not shown) when deployed in the body, so as to allow blood flow through the fenestration and into the branch vessel and/or to provide an opening through which a side arm or branch stent graft (not shown) can extend from the fenestration 150 formed in the stent graft 104 and into a branch vessel.

As illustrated in FIG. 2, the stent graft 104 can be radially expanded into the deployed configuration when the sheath 134 is withdrawn or retracted longitudinally in a distal direction. With the sheath 134 at least partially retracted to expose at least a portion of the stent graft 104, the stent graft 104 can radially expand. Alternatively or in addition to a sheath 134, one or more mechanisms may be further provided for retaining one or both ends of the stent graft in a radially compressed configuration and for securing the stent graft 104 to the introducer, including, but not limited to, diameter reducing ties, trigger wires, sutures and the like which would need to be removed before the stent graft 104 is permitted to fully expand and deploy.

In one example, the stent graft 104 comprises a self-expanding stent. A self-expanding stent may be manufactured from a shape-memory alloy, such as nickel titanium alloy (Nitinol). If the stent comprises a self-expanding material such as Nitinol, the stent may be heat-set into the desired expanded state whereby the stent can assume a relaxed radially expanded configuration. The stent may be made from other metals and alloys that allow the stent to return to its original expanded configuration upon deployment, such as, for example, stainless steel, cobalt-chrome alloys, amorphous metals, and/or non-metallic materials as would be recognized by one of skill in the art. Additionally or alternatively, the stent graft may be mechanically expanded, such as through the use of an expandable balloon placed within the lumen of the stent graft 104 and then radially outwardly expanded to thereby expand the stent graft 104. When the sheath 134 is distally retracted, the proximal end 124 of the pusher catheter 122 may configured to prevent the stent graft 104 from dislodging or sliding longitudinally away from its desired position on the inner cannula 108 at stent graft retention region 130.

As shown in FIG. 1, when in the delivery position, an opening 148 formed in the sheath 134 may be or may not be at least partially aligned transversely with the opening 144 of the pusher catheter 122. As shown in FIG. 2, during use, and upon at least partial distal retraction of the sheath 134, the sheath opening 148 may at least partially align longitudinally with the opening 144 of the pusher catheter 122 to allow an object, such as wire 152 to enter the lumen 126. In one example, when openings 148 and 144 are in alignment, a guide wire 152 may be inserted into the aligned openings 148, 144 to extend proximally through the pusher catheter lumen 126, into a distal end 160 of the stent graft 104 and through the fenestration 150. The sheath opening 148, pusher catheter opening 144, pusher catheter lumen 126, and/or the proximal opening 156 of the pusher catheter 122, can be sized to receive the wire 152. In one example, the sheath opening 148 and the pusher catheter opening 144 may be generally circular such that a longitudinal dimension is about the same as a transverse dimension. The sheath opening 148 and the pusher catheter opening 144 may be similar in size and dimension or alternatively, one of the respective openings 144, 148 may be larger or differently shaped and configured than the other of the openings.

The sheath opening 148 can also be at least partially aligned transversely with the opening 144 of the pusher catheter 122 when in the deployment position, as shown in FIG. 2. Thus, when in the deployment position, the lumen 126 can be accessible through the sheath opening 148 allowing wire 152 to be inserted through sheath opening 148 and pusher catheter opening 144, and then proximally into the pusher catheter lumen 126 and exit the proximal opening 156 of the pusher catheter 122. Thus, the wire 152 can be at least partially disposed within the lumen 126. After exiting the proximal opening 156 of the pusher catheter 122, the wire 152 may go through a portion of stent graft 104. As shown in FIG. 2, the wire 152 can extend though the opening or fenestration 150 in the stent graft 104 to enter a side branch of a vessel (not shown) to facilitate cannulation of the vessel side branch.

In conventional introducers, a wire may need to extend from the proximal end of the introducer through the distal end of the introducer. Here, however the wire 152 is able to extend out of the sheath opening 148 of the introducer 102. Therefore, the wire 152 does not need to extend all the way to the distal end of the introducer 102. Thus, the introducers described herein can be used with a relatively shorter wire 152 than conventional introducers. For instance, the length of the wire 152 can be reduced by about an amount equal to a distance between the sheath opening 148 and the distal end (not shown) of the introducer 102, thus enhancing control and accuracy and decreasing the time required to complete the medical procedure.

The lumen 126 can be used to access a branch vessel of a main vessel that the introducer 102 is within. In a non-limiting example, the lumen 126 may be used to facilitate cannulation of one or more renal arteries extending from the aorta, one or more common iliac arteries extending from the aorta, one or more internal iliac arteries extending from a common iliac artery and/or a subclavian, carotid or brachiocephalic artery extending from the aortic arch. A stent graft 104 may include multiple stent graft modules that are assembled in situ to form a prosthesis that extends from within the main vessel to within one or more branch vessels. For example, the stent graft 104 illustrated in FIGS. 1 and 2 can be a first prosthesis module, and the fenestration 150 can be configured to engage with a second prosthesis module (not shown).

As illustrated in FIG. 2, after the first prosthesis module has been deployed, the pusher catheter opening 144 and the sheath opening 148 can be aligned, and the wire 152 can be moved or pushed through the lumen 126 toward the fenestration 150. The wire 152 can exit the proximal end 156 of the pusher catheter and travel through at least a portion of the deployed stent graft 104. The wire 152 can be inserted through the fenestration 150 and navigated to a target site within the branch vessel. With the wire 152 still in the branch vessel, the introducer 102 may be withdrawn distally to remove the introducer 102 partially or completely from the main vessel. For instance, the introducer 102 may be slid off of the distal end of the wire 152, or the introducer 102 may be configured to be splittable and removable from the wire 152. A second introducer (not shown) that contains the second prosthesis module can then be slid over the wire 152 and navigated to the target site within the branch vessel. The second prosthesis module can then be deployed within the branch vessel and engaged with the first prosthesis module.

FIG. 3 shows the system of FIG. 1 in a partially deployed position. Compared with FIG. 2, the position of the sheath 134 in FIG. 3 is positioned more proximally and the pusher opening 144 and the sheath opening 148 are aligned differently. In particular, when the sheath is in the position of FIG. 3, sheath opening 148 and pusher opening 144 are at least partially aligned and a first portion 164 of the stent graft 104 has been deployed and has exited the sheath 134. A second portion 166 of the stent graft 104 remains within the sheath 134. The first portion 164 of the stent graft 104 can include a fenestration 150 such that the wire 152 can be navigated through the pusher catheter lumen 126 and through the fenestration 150 of the stent graft 104 when the sheath 134 has only been partially withdrawn.

FIG. 4 shows a longitudinal cross-sectional view of another exemplary delivery system for deploying a prosthesis within a body vessel. As shown in FIG. 4, the delivery system 100 includes an introducer 102 similar to the introducer 102 illustrated in FIG. 1 except that the sheath opening 148 comprises a longitudinal slot, elongated channel or slit. In particular, the sheath opening 148 extends longitudinally along a portion of the sheath 134 such that its longitudinal dimension is greater than a transverse dimension. Therefore, as the sheath 134 moves, the sheath opening 148 and the opening 144 formed in the pusher catheter 122 can remain aligned. For example, the sheath opening 148 and the opening 144 in the pusher catheter 122 may be aligned in both a delivery position when the sheath 134 is located proximally relative to the introducer and also in a deployment position when the sheath 134 has been at least partially or fully retracted in a distal direction.

For example, the opening 144 in the pusher catheter 122 can be aligned with a distal end 168 of the sheath opening 148 when in the delivery position, and the opening 144 in the pusher catheter 122 can be aligned with a proximal end 170 of the sheath opening 148 when the sheath has been distally retracted and the introducer 102 is in the deployment position. Thus, the wire 152 can be disposed through the opening 144 in the pusher catheter 122 and through the sheath opening 148 in both the delivery position and the deployment position.

In a variation of the example illustrated in FIG. 4, the sheath 134 may cover the opening 144 formed in the pusher catheter 122 when the introducer is in the delivery position, and the distal end 168 of the sheath opening 148 may be located proximal to the opening 144 in the pusher catheter 122. As the sheath is distally retracted, the stent graft 104 may then only be partially deployed when the proximal end 170 of the sheath opening 148 and the opening 144 in the pusher catheter 122 become aligned. The sheath opening 148 and the opening 144 in the pusher catheter 122 may then remain aligned during further distal retraction of the sheath 134 and deployment of the stent graft 104.

FIG. 5 illustrates another example of a delivery system 100 wherein the pusher catheter 122 further includes a valve 172 extending from the opening 144 in the pusher catheter 122. The lumen 126 of the pusher catheter 122 can extend through the sheath opening 148, while the valve 172 can provide a seal to prevent fluid from flowing back through the opening 144 in the pusher catheter 122. For example, the valve 172 can be a resealable membrane, slit, septum and the like that provides a barrier while also permitting an object such as wire 152 to penetrate the membrane. The wire 152 may be pre-loaded within the system 100 so that it is at least partially disposed within the lumen 126 when the introducer is in the delivery position.

Figure 6:
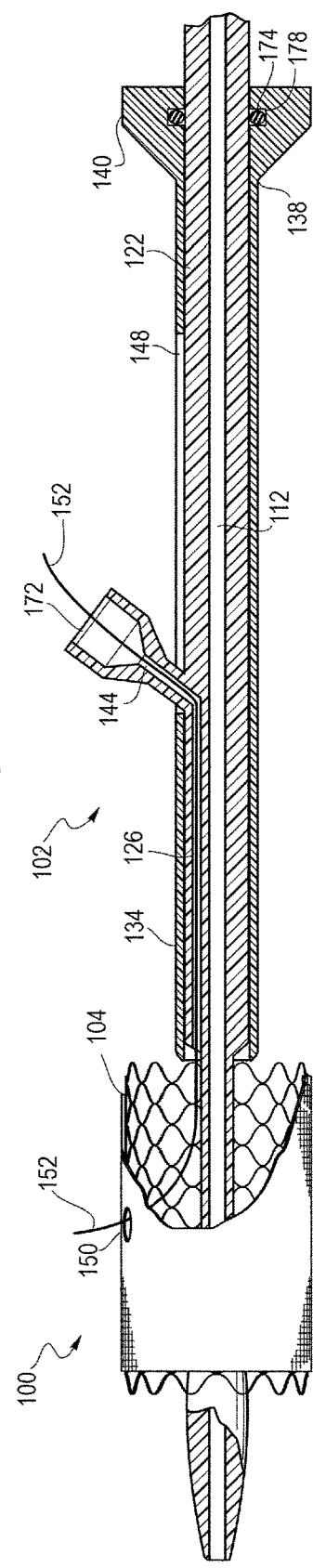
FIG. 6 shows the system of FIG. 5 in a deployment configuration.

FIG. 5 shows the system 100 in the delivery configuration, with the sheath 134 covering the stent graft 104 and the valve 172 positioned at the distal end of the opening/slot 148 formed in the sheath 134. FIG. 6 shows the system 100 of FIG. 5 in a deployment position, where the sheath 134 has been withdrawn distally to expose the stent graft 104 with the valve 172 now being located at a proximal end of the opening/slot 148 formed in the sheath 134. Furthermore, the wire 152 may be extended proximally through the lumen 126 and through the fenestration 150 formed in the stent graft when the stent graft 104 has been at least partially deployed.

FIG. 7 shows a longitudinal cross-sectional view of another example of a delivery system 100 for deploying a prosthesis within a body vessel. The introducer 102 includes one or more seals 174 to provide hemostasis within the system, so that fluid is prevented from flowing back through the sheath opening 148 when the introducer 102 is in the delivery position. The seal 174 can be an annular sealing member such as a silicone ring that extends circumferentially around the pusher catheter 122. Additionally, a seal 174 can be disposed between the pusher catheter 122 and the sheath 134. The seal 174 may be positioned adjacent to the sheath opening 148 as shown in an enlarged view in FIG. 7B and a seal 174 may also be positioned adjacent the opening 144 in the pusher catheter 122 as shown in an enlarged view in FIG. 7C.

For example, the seal 174 can be proximal to the sheath opening 148 to restrict fluid flow entering through a passageway 176 at the proximal end of the sheath 134 to the sheath opening 148. In another example, the seal 174 can be proximal to the opening 144 in the pusher catheter 122 to restrict fluid flow from the lumen 126 to the sheath opening 148. In an even further example, the seal 174 can be distal to the opening 144 in the pusher catheter 122 to restrict fluid flow from the lumen 126 of the pusher catheter 122 to the distal end 138 of the sheath 134.

The sidewall 154 of the sheath 134 or the sidewall 128 of the pusher catheter 122 may include an annular slot 178 that the seal 174 is disposed at least partially within. Thus, when the sheath 134 is longitudinally moved relative to the pusher catheter 122, the annular slot 178 can restrict longitudinal movement of the seal 174 relative to the annular slot 178, thus maintaining a seal with the pusher catheter 122 when the handle 140 and sheath 134 move longitudinally relative to the pusher catheter 122. In a further example, the introducer 102 may include a hemostatic valve (not shown) at the distal end 138 of the sheath 134 and/or within handle 140. The hemostatic valve can restrict and/or prevent fluid flow from exiting the distal end 138 of the sheath 134. For example, the hemostatic valve can include an annular seal similar to that discussed above with regard to the other seals 174.

FIG. 8 shows a longitudinal cross-sectional view of another example of a delivery system 100 for deploying a prosthesis within a body vessel. The introducer 102 illustrated in FIG. 8 is similar to the introducer 102 illustrated in FIGS. 1 and 2 except that the lumen 126 of the pusher catheter 122 further extends longitudinally beyond the opening 144 in the pusher catheter 122 toward the distal end (not shown).

FIG. 8 illustrates the introducer 102 in the delivery position, with the stent graft 104 held in a radially inwardly constricted configuration by the sheath 134. The lumen 126 of the pusher catheter 122 may extend to the distal end (not shown) of the pusher catheter 122 (e.g., the lumen extends from the proximal end 124 of the pusher catheter 122 to the distal end), or the lumen 126 may extend to a position located between the opening 144 and the distal end in the pusher catheter 122. For example, the lumen 126 may extend distal to opening 144 but not extend all the way to the distal end of the pusher catheter 122.

One or more wires 152 can be preloaded at least partially within the lumen 126 of the pusher catheter 122 prior to the introducer 102 being inserted into the body vessel. In particular, a portion of the wire 152 can be disposed within the lumen 126 of the pusher catheter 122 that is distal to the opening 144 in the pusher catheter 122, and another portion of the wire 152 can be disposed within the lumen 126 that is proximal to the opening 144 in the pusher catheter 122. In one example, the portion of the lumen 126 that is distal to the opening 144 in the pusher catheter 122 can serve as a storage region for the distal portion of the wire 152 during delivery of the introducer 102 into the body vessel.

FIG. 9 shows the system of FIG. 8 in a deployment position. In FIG. 9, the introducer 102 is in the deployment position with sheath 134 distally withdrawn to expose the stent graft 104 and allow the stent graft to deploy. The sheath opening 148 and the opening 144 in the pusher catheter 122 are aligned. The wire 152 can be moved proximally out of the proximal end 124 of the pusher catheter 122, and the wire 152 can be moved through a fenestration 150 in the stent graft 104.

FIG. 10 also shows the system of FIG. 8 in a deployment position. As shown in FIG. 10, a distal portion 182 of the wire 152 can be pulled through the aligned opening 144 in the pusher catheter 122 and the sheath opening 148. The distal portion 182 of the wire 152 may be pulled through the opening 144 in the pusher catheter 122 and the sheath opening 148 prior to substantially moving the wire 152 longitudinally. Alternatively, the wire 152 may be moved at least partially prior to pulling the distal portion 182 of the wire 152 through the opening 144 in the pusher catheter 122 and the sheath opening 148. After the distal portion 182 of the wire 152 is removed from the lumen 126 of the pusher catheter 122, the wire 152 can be manipulated by controlling the distal portion 182. For example, by manipulating the distal portion 182 or the wire, a proximal portion 184 of the wire 152 can be moved proximally through the lumen 126 of the pusher catheter 122 and through the fenestration 150 formed in the stent graft 104.

The pusher catheter 122 may also include an inner cannula lumen 112 configured to receive a guide wire (not shown) there through. For example, a guide wire may be navigated to a target site within a patient. The introducer 102 can be tracked over the guide wire so that guide wire is at least partially disposed within the inner cannula lumen 112. The introducer 102 can then follow the guide wire to the target site for deployment of the stent graft 104. However, the pusher catheter 122 may have multiple lumens as generally described herein. Alternatively, the pusher catheter 122 may have a single lumen to receive the guide wire (not shown) for tracking the system to a desired position within a body vessel and/or to also receive the wire 152 and/or other wires, cannulas or catheters as necessary or desired depending on the particular procedure being performed.

FIG. 11 shows a longitudinal cross-sectional view of another exemplary delivery system for deploying a prosthesis within a body vessel. FIG. 11 illustrates a system 100 that includes an introducer 102 that has a single lumen 112. The functions of the lumen 112 for the wire 152 and the lumen 112 for the guide wire (not shown) have been combined into one lumen 112. The introducer 102 can slide over a guide wire extending through the lumen 112 such that the guide wire extends at least from the nose cone 114 to the proximal end 124 of the pusher catheter 122. The guide wire can be removed from the lumen 112 after the introducer 102 has reached the target site within the patient.

The introducer 102 can be moved from the delivery position to the deployment position by retracting the sheath 134 thereby deploying the stent graft 104 and thus aligning the sheath opening 148 and opening 144 in the pusher catheter 122. The wire 152 can then be inserted through the aligned sheath opening 148 and opening 144 in the pusher catheter 122 and into the lumen 112. The wire 152 can be tracked through the lumen 112 proximally into the nose cone 114. The introducer 102 may be moved distally relative to the deployed stent graft 104 so that the nose cone 114 is pulled within the stent graft 104 so that the wire 152 can enter the fenestration 150 in the stent graft 104. Although the pusher catheter 122 in FIG. 11 is illustrated having a single lumen 112, the pusher catheter 122 may include other lumens (not shown) for additional functions.

FIG. 12 shows a longitudinal cross-sectional view of another exemplary delivery system for deploying a prosthesis within a body vessel. The pusher catheter 122 further includes a groove 186 formed in the sidewall 128 that extends longitudinally from the opening 144 in the pusher catheter 122 toward the distal end (not shown) of the pusher catheter 122. For example, the groove 186 can extend from the opening 144 in the pusher catheter 122 to a position between the opening 144 in the pusher catheter 122 and the distal end (not shown) of the pusher catheter 122. Alternatively the groove 186 can extend from the opening 144 in the pusher catheter 122 to a position located between the opening 144 in the pusher catheter 122 and the distal end 138 of the sheath 134. The groove 186 can be sized to receive a wire, such as wire 152.

The wire 152 can be pre-loaded within the lumen 126 of the pusher catheter 122 and the groove 186 prior to delivery into the body vessel. The groove 186 is illustrated as having a similar longitudinal length as the lumen 126 of the pusher catheter 122; however, the groove 186 can have a longitudinal length different from the longitudinal length of the lumen 126 of the pusher catheter 122. For example, the longitudinal length of the groove 186 may be greater than the longitudinal length of the lumen 126 of the pusher catheter 122.

FIG. 13 shows the system of FIG. 12 with the sheath 134 partially withdrawn and the stent graft 104 in a partially deployed position. The sheath opening 148 and the opening 144 in the pusher catheter 122 can be positioned such that they become aligned when the stent graft 104 is only partially deployed, as illustrated in FIG. 13. In addition, the sheath opening 148 and the opening 144 in the pusher catheter 122 can be positioned so that they become aligned when the stent graft 104 is completely deployed.

When the sheath opening 148 and the opening 144 in the pusher catheter 122 are aligned, the wire 152 can be pulled through the opening 144 in the pusher catheter 122 and the sheath opening 148. For example, as illustrated in FIG. 13, a suture 188, comprising a cord, string or wire or other suitable attachment mechanism can be wrapped at least partially around the wire 152. The suture 188 can extend out of the opening 144 in the pusher catheter 122 and the sheath opening 148. The suture 188 may also be pre-loaded in the system 100 along with the wire 152. For example, the suture 188 can be configured to extend out of the sheath opening 148 when the opening 144 in the pusher catheter 122 and the sheath opening 148 are aligned. Alternatively, the wire 152 may not be pre-loaded, and instead, the wire 152 may be inserted through the aligned opening 144 in the pusher catheter 122 and the sheath opening 148, and the suture 188 may then be wrapped at least partially around the wire 152.

FIG. 14 shows the system of FIG. 13 with the stent graft 104 in a partially deployed position. As illustrated in FIG. 14, the suture 188 has been pulled out to facilitate removal of the distal portion 182 of the wire 152 from the groove 186 formed in the sidewall 128 of the pusher catheter 122. In this configuration, the distal end 182 of the wire 152 is now accessible.

Figure 15:
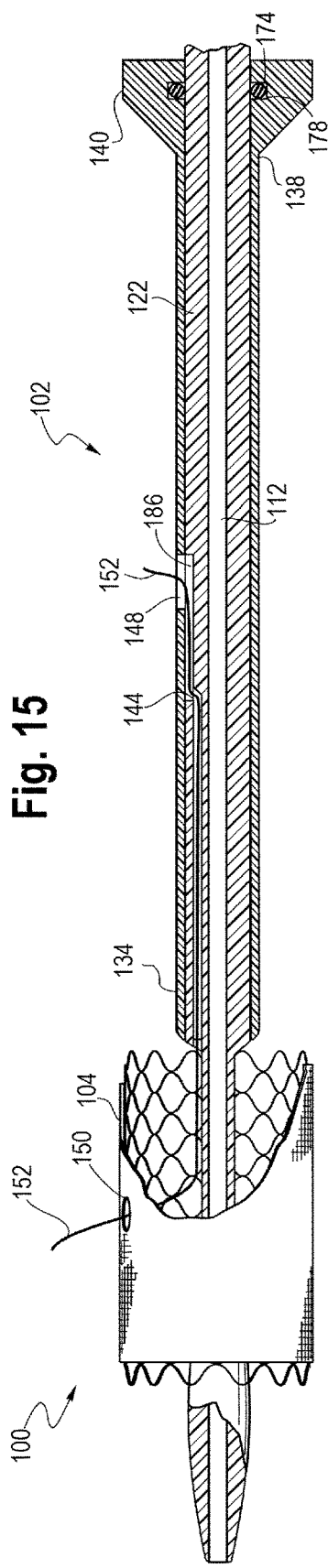
FIG. 15 shows the system of FIG. 12 in a fully deployed configuration.

FIG. 15 shows the system of FIG. 12 with the stent graft 104 in a fully deployed position. When in a full deployment position, the sheath opening 148 may be at least partially longitudinally aligned with the groove 186. The groove 186 permits the sheath 134 to move further longitudinally distally after alignment of the sheath opening 148 and the opening 144 in the pusher catheter 122 while the wire 152 extends through the sheath opening 148 and the lumen 126 of the pusher catheter 122. Thus, the wire 152 can be manipulated by a user when the stent graft 104 is partially deployed (as shown in FIG. 14) and when the stent graft 104 is fully deployed (as shown in FIG. 15).

Figure 16:
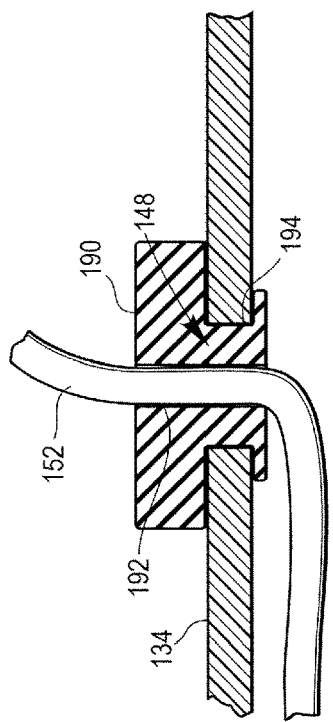
FIG. 16 shows an enlarged longitudinal cross-sectional view of an exemplary sheath opening.

FIG. 16 shows an enlarged longitudinal cross-sectional view of an exemplary sheath opening. In this example, a seal ring 190 is disposed at least partially within the sheath opening 148. The seal ring 190 can provide a fluid seal between the sheath 134 and the wire 152 to provide hemostasis. The seal ring 190 can include a through-hole, aperture, septum 192 or similar re-sealable membrane so that the wire 152 can extend through the through-hole 192. The through-hole 192 can be configured to self-close such that the seal ring 190 provides a fluid seal even when the wire 152 does not extend through the through-hole 192. The seal ring 190 may include a slot 194 formed in an outer circumference of the seal ring 190 that engages with the sheath 134 around the sheath opening 148. The seal ring 190 can be disposed within any of the sheath openings 148 described herein. However, in one example, the seal ring 190 can be self-closing and disposed in the sheath opening 148 to fluidly isolate the lumen 126 from the sheath opening 148.

FIG. 17 shows a longitudinal cross-sectional view of another exemplary delivery system for deploying a prosthesis within a body vessel. The introducer 102 can include two or more lumens 126. More than one lumen 126 may be desirable when more than one branch of a body vessel requires a prosthesis module to be delivered to and deployed within. Thus, any of the introducers 102 described herein can include a first lumen 126*a* and a second lumen 126*b*.

The first lumen 126*a* and the second lumen 126*b* can be spaced apart from one another and run parallel within the pusher catheter 122. For example, the first lumen 126*a* may run parallel to lumen 112 on a first side of the pusher catheter 122 and the second lumen 126*b* may run parallel within the pusher catheter 122 on a second side opposite to the first side as shown in FIG. 17. Furthermore, the first lumen 126*a* and the corresponding portion of the sheath 134 that is adjacent to the first lumen 126*a* may be configured similar or different to the second lumen 126*b* and the corresponding portion of the sheath 134 that is adjacent to the second lumen 126*b*. For example, the first lumen 126*a* may extend between a first proximal pusher catheter opening 156*a* and a first opening 144*a* in pusher catheter 122, and the second lumen 126*b* may extend between a second proximal pusher catheter opening 156*b* and a second opening 144*b* in pusher catheter 122 as shown in FIG. 17. The sheath 134 may have a first sheath opening 148*a* that corresponds to the first opening 144*a* in pusher catheter 122, and a second sheath opening 148*b* that corresponds to the second opening 144*b* in pusher catheter 122.

When in the delivery position as shown in FIG. 17, the first sheath opening 148*a* and the first opening 144*a* in pusher catheter 122 may not be aligned, and the second sheath opening 148*b* and the second opening 144*b* in pusher catheter 122 may not be aligned. When the sheath 134 is distally retracted and the introducer 102 is in the deployment position, the first sheath opening 148*a* and the first opening 144*a* in pusher catheter 122 may become aligned, and the a second sheath opening 148*b* and the second opening 144*b* in pusher catheter 122 may become aligned.

Alternatively, the introducer 102 may have a first deployment position and a second deployment position. When in the first deployment position, the first sheath opening 148*a* and the first opening 144*a* in pusher catheter 122 may be aligned, and the second sheath opening 148*b* and the second opening 144*b* in pusher catheter 122 may not be aligned. When in the second deployment position, the first sheath opening 148*a* and the first opening 144*a* in pusher catheter 122 may not be aligned, and the second sheath opening 148*b* and the second opening 144*b* in pusher catheter 122 may be aligned.

FIG. 18 shows an enlarged side-elevation cross-sectional view of a portion of the system of FIG. 17. More particularly, it can be seen in FIG. 18 that the introducer 102 can include two or more lumens 126*a* and 126*b*. As shown in FIG. 18, the first lumen 126*a* and a second lumen 126*b* may be configured to receive one or more wires 152 there through.

FIG. 19 shows the system of FIG. 18 with the sheath distally retracted. The sheath opening 148*a* and the opening 144*a* in the pusher catheter 122 are aligned. In addition, the sheath opening 148*b* and the opening 144*b* in the pusher catheter 122 are aligned. A suture 188 can extend out of the opening 144*a* and/or 144*b* in the pusher catheter 122 and through the sheath openings 148*a* and/or 148*b*. The suture 188 may be pre-loaded in the system 100 along with the wire 152. For example, the suture 188 can be configured to extend out of the sheath openings 148*a* and/or 148*b* when the openings 144a and/or 144b in the pusher catheter 122 and the sheath openings 148a and/or 148b are aligned. Alternatively, the wire 152 may not be pre-loaded, and instead, the wire 152 may be inserted through the aligned openings 144a and/or 144b in the pusher catheter 122 and the sheath openings 148 and/or 148b, and the suture 188 may be wrapped at least partially around the wire 152.

When the sheath opening 148a and the opening 144a in the pusher catheter 122 are aligned, the wire 152 can be pulled through the opening 144a in the pusher catheter 122 and the sheath opening 148a. For example, as illustrated in FIG. 19, a suture 188 such as a string or wire can be wrapped at least partially around the wire 152 extending within lumen 126a. Similarly, when the sheath opening 148b and the opening 144b in the pusher catheter 122 are aligned, a wire 152 can be pulled through the opening 144b in the pusher catheter 122 and the sheath opening 148b. For example, as illustrated in FIG. 19, a suture 188 such as a string or wire can be wrapped at least partially around the wire 152 extending within lumen 126b.

FIG. 20 shows the system of FIG. 19 with the sheath further distally retracted. The sheath opening 148a and the opening 144a in the pusher catheter 122 may still be aligned. In addition, the sheath opening 148b and the opening 144b in the pusher catheter 122 may still be aligned. When the sheath opening 148a and the opening 144a in the pusher catheter 122 are aligned, wire 152 can be pulled through the opening 144a in the pusher catheter 122 and the sheath opening 148a. Similarly, when the sheath opening 148b and the opening 144b in the pusher catheter 122 are aligned, a wire 152 can be pulled through the opening 144b in the pusher catheter 122 and the sheath opening 148b. As shown in FIG. 20, the distal end 182 of the wire 152 may then be accessible.

FIG. 21 shows the system of FIG. 20. The sheath opening 148a and the opening 144a in the pusher catheter 122 are aligned with wire 152 pulled through the opening 144a in the pusher catheter 122 and the sheath opening 148a. Similarly, wire 152 is pulled through the opening 144b in the pusher catheter 122 and the sheath opening 148b. Similar to the seal 190 described in connection with FIG. 16. FIG. 21 illustrates that a seal ring 196 may be coupled to sheath opening 148a and/or 148b. In one example, the seal may be a seal ring 196 disposed at least partially within the sheath opening 148. The seal ring 196 can provide a fluid seal between the sheath 134 and the wire 152 to provide hemostasis. The seal ring 196 can include a through-hole, aperture, septum or similar re-sealable membrane so that the wire 152 can extend through the through-hole. The through-hole can be configured to self-close such that the seal ring 196 provides a fluid seal even when the wire 152 does not extend through the through-hole. The seal ring 196 may include a slot 194 formed in an outer circumference of the seal ring 196 that engages with the sheath 134 around the sheath opening 148a and or 148b. The seal ring 196 can be disposed within any of the sheath openings 148 described herein to fluidly isolate the lumen 126 from the sheath opening 148.

FIG. 21B shows an enlarged view of the seal ring shown in FIG. 21.

The delivery device 100 and its various components including but not limited to the introducer including the pusher catheter 122 and the guide wire lumen 112 formed there through can be formed in an extrusion process such as polymer extrusion. The opening 144 in the pusher catheter 122 can be formed after the extrusion process. For example, the opening 144 in the pusher catheter 122 can be formed by machining or drilling through the sidewall 128 of the pusher catheter 122 to the lumen 112. Furthermore, the pusher catheter 122 and the one or more lumen(s) 126 can also be formed by an extrusion process. The lumen(s) 126 may not be formed when the pusher catheter 122 is extruded. For example, the lumen(s) 126 may be machined or drilled after the pusher catheter 122 is extruded. The groove 186 can also be formed after extrusion of the pusher catheter 122 such as by machining. Thus, the extrusion process may be simplified by reducing the number of lumens co-extruded with the pusher catheter 122.

Figure 22:
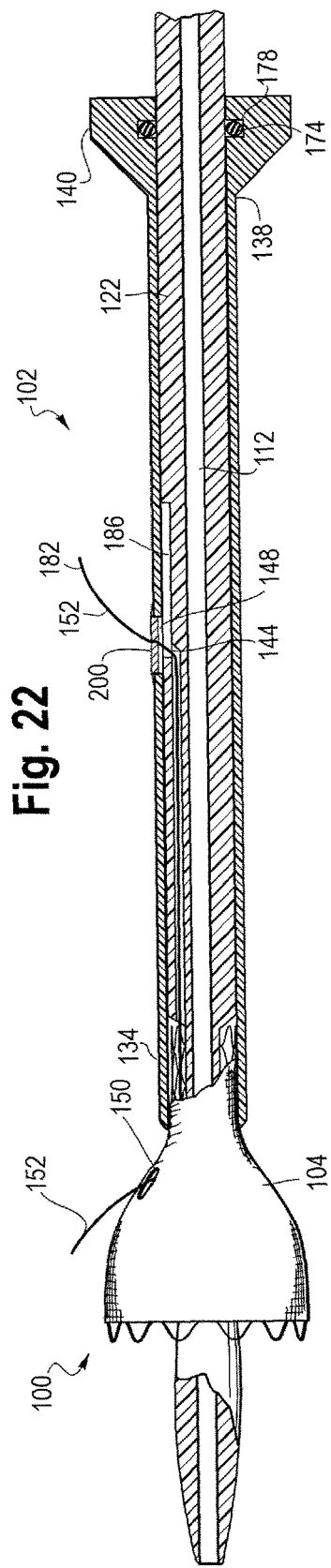
FIG. 22 shows a longitudinal cross-sectional view of an exemplary delivery system for deploying a prosthesis within a body vessel in a partially deployed configuration.

FIG. 22 shows a longitudinal cross-sectional view of an exemplary delivery system for deploying a prosthesis within a body vessel in a partially deployed configuration. The system shown in FIG. 22 is similar to the systems described above except that a membrane 200 may at least partially cover opening 148 in the sheath 134. The membrane 200 may be penetrable or puncturable. In one example, the membrane 200 may be punctured by wire 152. The membrane 200 may be self-sealing. In other words, when the membrane 200 is punctured by wire 152, it may maintain a tight seal. Further, when wire 152 or another object is removed from the membrane 200, the membrane 200 may be able to keep sealed. As a result, any fluid flowing distally through the sheath 134 may be prevented from flowing through the membrane 200.

In one example, the membrane 200 is made of biocompatible material, including but not limited to Silicone, Thoralon, SBS (Styrene Butadiene Styrene), Synthetic Polyisoprene, Latex, fluorosilicone, Thermoplastic Elastomers (including thermoplastic polyurethanes (TPU), Theromoplastic copolyester, Thermoplastic polyamides, styrenic block copolymers (TPE-s), Thermoplastic olefins (TPE-s), Elastomeric alloys (TPE-v or TPV)), elastomeric silicones (including LSR Liquid Silicone Rubber Durometer having a range 5 Shore A to 50 Shore a; HCR High Consistency Rubber Durometer having a range 10 Shore A to 50 Shore A; Flurosilicones), and rubbers such as EPDM and BUNA. In one example, the membrane 200 may be constructed of Thoralon, which allows the membrane 200 to seal by clotting in combination with its elasticity. Membrane 200 may be any color or colorless. In one example, membrane 200 is clear or translucent.

Figure 23:
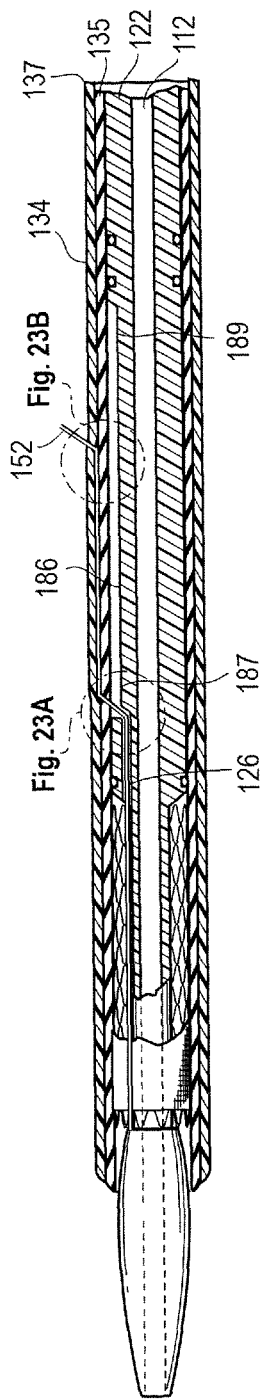
FIG. 23 shows a longitudinal cross-sectional view of an exemplary delivery system for deploying a prosthesis within a body vessel in a deployment configuration.
Figure 23B:
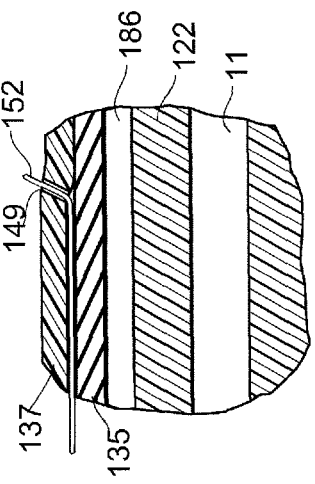
FIG. 23B shows an enlarged view of a portion of FIG. 23 where the wire exits the sheath.
Figure 23A:
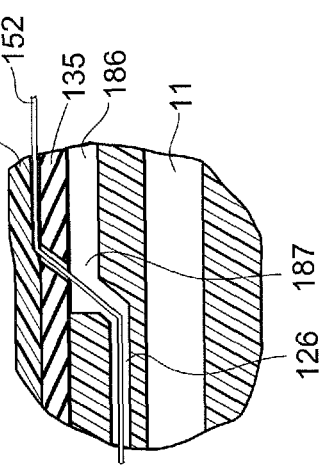
FIG. 23A shows an enlarged view of a portion of FIG. 23.

FIG. 23 shows a longitudinal cross-sectional view of an exemplary delivery system for deploying a prosthesis within a body vessel. FIG. 23A shows an enlarged view of a portion of FIG. 23. FIG. 23B shows an enlarged view of a portion of FIG. 23 where the wire exits the sheath. FIG. 23 is similar to the system described earlier and shown in FIG. 12 except that the introducer sheath 134 may further be comprised of two layers: inner layer 135 and outer layer 137. The sheath 134 can be configured to receive a wire 152. The wire 152 can be at least partially disposed longitudinally between inner layer 135 and outer layer 137. One benefit of having the wire 152 at least partially longitudinally disposed between inner layer 135 and outer layer 137 is that the path through the sheath 134 layers 135, 137 creates hemostasis.

The wire 152 can be pre-loaded within the lumen 126 of the pusher catheter 122 prior to delivery into the body vessel. The wire 152 may extend out of an opening in the pusher catheter 122 and into the inner layer 135 of the sheath 134. The wire may be at least partially disposed longitudinally between the inner layer 135 and outer layer 137 of the sheath 134 and may exit the outer layer 137 of the sheath 134 through an opening 149 in the outer layer 137 of the sheath 134.

Figure 24:
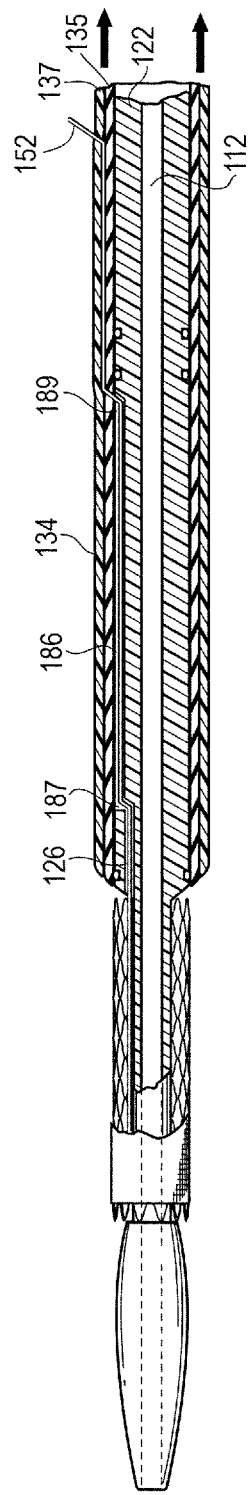
FIG. 24 shows a longitudinal cross-sectional view of the system of FIG. 23 with the sheath withdrawn.

FIG. 24 shows a longitudinal cross-sectional view of the system of FIG. 23 with the sheath 134 withdrawn distally. In one example, the wire 152 may extend longitudinally between the inner layer 135 and outer layer 137 of the sheath 134 as well as from the proximal end 187 of groove 186 to the distal end 189 of groove 186.

Figure 25:
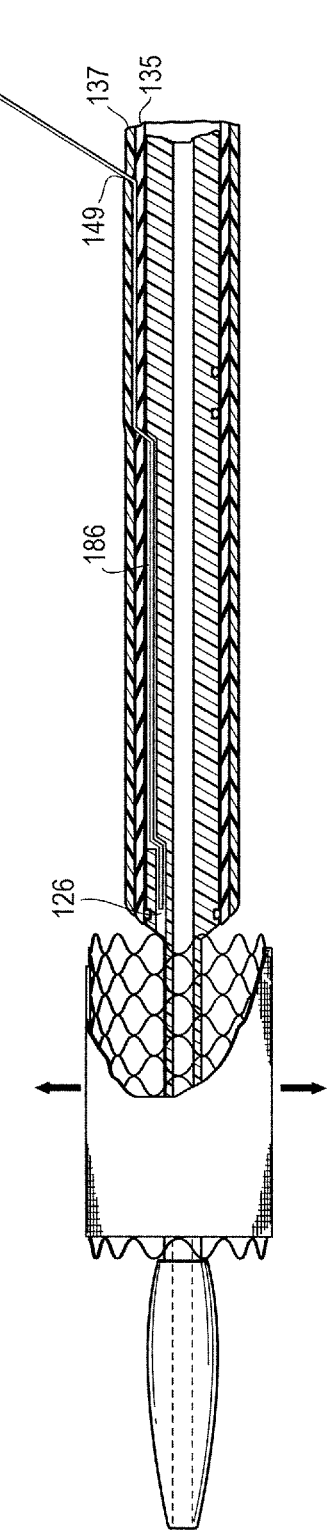
FIG. 25 shows the system of FIG. 23 in a deployment configuration.

FIG. 25 shows the system of FIG. 23 in a deployment configuration. When the sheath 134 has been withdrawn distally and the stent graft 104 is in a full deployment position, the wire 152 may be disposed at least partially in the groove 186. The preloaded wire 152 can extend from the lumen 126 of the pusher catheter 122 to opening 144 in the pusher catheter 122. The wire 152 may extend into the groove 186 and into the inner layer 135 of the sheath 134. The wire may be at least partially disposed longitudinally between the inner layer 135 and outer layer 137 of the sheath 134 and may exit the outer layer 137 of the sheath 134 through an opening 149 in the outer layer 137 of the sheath 134. In one example, the wire 152 may extend longitudinally between the inner layer 135 and outer layer 137 of the sheath 134 from approximately the same length as the groove 186.

FIG. 26 shows the system of FIG. 23 with a valve 172 extending from the opening 149 in the outer layer 137 of the sheath 134. The valve 172 may slide over sheath 134 to create hemostasis. The valve 172 can provide a seal to prevent fluid from flowing back through the sheath 134 and into the opening 144 in the pusher catheter 122. For example, the valve 172 can be a resealable membrane, slit, septum and the like that provides a barrier while also permitting an object such as wire 152 to penetrate the membrane. The wire 152 may be pre-loaded within the system 100 so that it is at least partially disposed within the pusher catheter lumen 126 when the introducer is in the delivery position.

FIG. 27 shows the system of FIG. 26 in a deployment configuration. FIG. 27 shows the system 100 of FIG. 26 in a deployment position, wherein the sheath 134 is withdrawn distally to expose the stent graft 104. The wire 152 may extend proximally through the valve 172, through the outer layer 137 of the sheath 134, longitudinally between the outer layer 137 and inner layer 135 of the sheath. The wire may extend through at least a portion of the groove 186 and lumen 126 of the pusher catheter.

Figure 28:
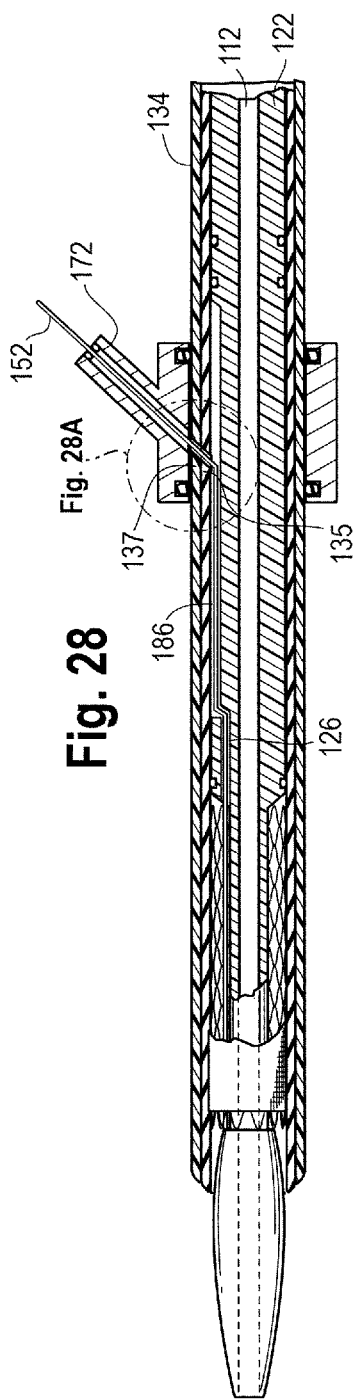
FIG. 28 shows a longitudinal cross-sectional view of an exemplary delivery system for deploying a prosthesis within a body vessel.
Figure 28A:
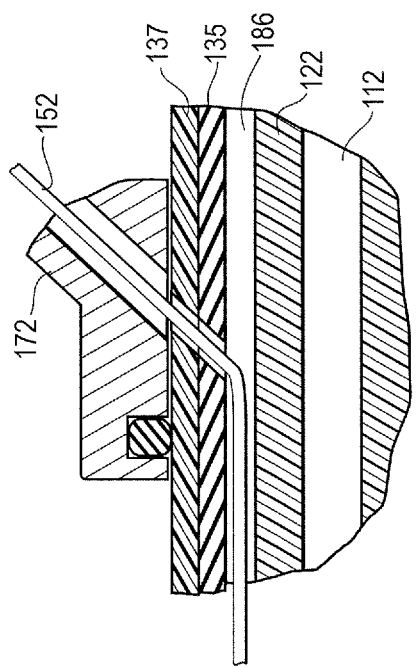
FIG. 28A shows an enlarged view of a portion of FIG. 28 where the wire is disposed in the valve.

FIG. 28 shows a longitudinal cross-sectional view of an exemplary delivery system for deploying a prosthesis within a body vessel. The system shown in FIG. 28 is similar to the system shown in FIG. 26 except that the wire 152 may cut a straight path through inner layer 135 and outer layer 137 of the sheath 134 and into groove 186. Using the wire 152 to cut a shorter path through the sheath can create a tighter seal.

While various embodiments of the invention have been described, the invention is not to be restricted except in light of the attached claims and their equivalents. Moreover, the advantages described herein are not necessarily the only advantages of the invention.

We claim:

1. An introducer for an endoluminal prosthesis comprising:
    an inner cannula having a proximal end and a distal end and a prosthesis releasably attached to the proximal end of the inner cannula;
    a pusher catheter disposed about at least a portion of the inner cannula, the pusher catheter having a proximal end a distal end and a side wall extending between the proximal and distal ends of the pusher catheter, the side wall comprising an opening formed therein,
    a lumen extending at least partially through the pusher catheter between the proximal and distal ends of the pusher catheter, the pusher catheter lumen being in communication with the opening formed in the side wall of the pusher catheter; and
    a tubular sheath disposed coaxially about at least a portion of the pusher catheter, the tubular sheath having a proximal end, a distal end, a sidewall extending between the proximal and distal ends of the tubular sheath and an opening formed in the sidewall of the tubular sheath;
    wherein the tubular sheath is longitudinally movable relative to the pusher catheter between a prosthesis delivery position and a prosthesis deployment position, wherein the pusher catheter further comprises a port that extends radially outwardly from the sidewall of the pusher catheter and wherein the port is in fluid communication with the opening formed in the side wall of the pusher catheter.

2. The introducer of claim 1, wherein when the tubular sheath is in the prosthesis deployment position, the opening formed in the sidewall of the pusher catheter is at least partially longitudinally aligned with the opening formed in the sidewall of the tubular sheath.

3. The introducer of claim 1, wherein the opening formed in the sidewall of the tubular sheath comprises a slot extending longitudinally along at least a portion of the tubular sheath such that the slot formed in the tubular sheath and the opening formed in the sidewall of the pusher catheter are longitudinally aligned when the tubular sheath is in both the delivery position and in the deployment position.

4. The introducer of claim 1, wherein the pusher catheter further comprises a second opening formed in the sidewall of the pusher catheter.

5. The introducer of claim 1, wherein the pusher catheter further comprises a second lumen extending at least partially through the pusher catheter between the proximal and distal ends of the pusher catheter, the second pusher catheter lumen being in communication with the second opening formed in the side wall of the pusher catheter.

6. The introducer of claim 5, wherein the second pusher catheter lumen extends from the proximal end of the pusher catheter to the second opening formed in the sidewall of the pusher catheter.

7. The introducer of claim 5, wherein the tubular sheath comprises a second opening formed in the sidewall of the tubular sheath.

8. The introducer of claim 7, wherein when the tubular sheath is in the deployment position, the second opening formed in the sidewall of the tubular sheath is at least partially longitudinally aligned with the second opening formed in the sidewall of the pusher catheter.

9. The introducer of claim 1, further comprising at least one annular sealing member disposed between the pusher catheter the tubular sheath.

10. The introducer of claim 1, further comprising a seal disposed within the opening formed in the sidewall of the tubular sheath.

11. The introducer of claim 1, wherein a wire is disposed longitudinally within at least a portion the pusher catheter lumen.

12. The introducer of claim 11, wherein the prosthesis further comprises at least one fenestration formed therein and wherein when the tubular sheath is in the deployment position, the wire extends through the opening formed in the side wall of the tubular sheath and through the opening formed in the sidewall of the pusher catheter, further extends proximally through the pusher catheter lumen and through the fenestration formed in the prosthesis.

* * * * *